United States Patent [19]

Schwan

[11] 4,205,172

[45] May 27, 1980

[54] 7,10-DICHLORO-3-METHYL-4-PHENYL-1,2,3,4-TETRAHYDROBENZ[H]ISOQUINOLINE HYDROBROMIDE

[75] Inventor: Thomas J. Schwan, Norwich, N.Y.

[73] Assignee: Morton-Norwich Products, Inc., Norwich, N.Y.

[21] Appl. No.: 1,610

[22] Filed: Jan. 8, 1979

[51] Int. Cl.[2] .................... C07D 221/10; A61K 31/47
[52] U.S. Cl. ..................................... 546/101; 424/258
[58] Field of Search ........................ 546/101; 424/258

[56] References Cited

U.S. PATENT DOCUMENTS

| | | | |
|---|---|---|---|
| 3,940,400 | 2/1976 | Schwan | 546/101 |
| 4,081,543 | 3/1978 | Bastion | 546/101 X |
| 4,115,387 | 9/1978 | Schwan | 546/101 |

*Primary Examiner*—Donald G. Daus
*Assistant Examiner*—Diana G. Rivers
*Attorney, Agent, or Firm*—Anthony J. Franze

[57] ABSTRACT

The compound 7,10-dichloro-3-methyl-4-phenyl-1,2,3,4-tetrahydrobenz[h]isoquinoline hydrobromide is useful as an antifungal agent.

1 Claim, No Drawings

7,10-DICHLORO-3-METHYL-4-PHENYL-1,2,3,4-TETRAHYDROBENZ[H]ISOQUINOLINE HYDROBROMIDE

The invention is concerned with the compound 7,10-dichloro-3-methyl-4-phenyl-1,2,3,4-tetrahydrobenz[h]isoquinoline hydrobromide. At a concentration of 40 μg/ml and 100 μg/ml in Sabourand's dextrose broth it inhibits the growth of *Candida albicans* and *Microsporum canis*, respectively, in the commonly employed agar diffusion test. It is adapted to be combined in various forms such as elixirs, dust, unguents, solutions and suspensions to provide compositions inimical to fungal growth.

In order that this invention may be readily available to and understood by those skilled in the art, the following preparation is supplied.

7,10-Dichloro-3-methyl-4-phenyl-1,2,3,4-tetrahydrobenz[h]isoquinoline hydrobromide To 34.0 g (0.0944 mole) of 2-(5,8-dichloro-1-naphthylmethylamino)-1-phenyl-1-propanol free base was added cautiously 250 ml 48% HBr. The mixture was stirred and refluxed for sixty hours, cooled and the resulting solid was filtered through a medium sintered glass funnel. The solid was washed with 3×75 ml $H_2O$, air dried for three hours, washed with 3×125 ml ethyl acetate, and air dried. The product weighed 27.9 g (70%) and melted at 298–310°. An analytical sample, m.p. 313–317°, was obtained by recrystallization from methanol.

Anal. calcd. for $C_{20}H_{17}Cl_2N \cdot HBr$: C, 56.76; H, 4.29; N, 3.31. Found: C, 56.87; H, 4.23; N, 3.12.

What is claimed is:

1. The compound 7,10-dichloro-3-methyl-4-phenyl-1,2,3,4-tetrahydrobenz[h]isoquinoline hydrobromide.

* * * * *